United States Patent [19]

Broughton

[11] 4,306,107
[45] Dec. 15, 1981

[54] PRODUCTION OF PURE M-XYLENE AND PURE ETHYL BENZENE FROM A MIXTURE OF C8 AROMATIC ISOMERS

[75] Inventor: Donald B. Broughton, Evanston, Ill.

[73] Assignee: UOP Inc., Des Plaines, Ill.

[21] Appl. No.: 144,757

[22] Filed: Apr. 28, 1980

Related U.S. Application Data

[63] Continuation-in-part of Ser. No. 123,227, Feb. 7, 1980.

[51] Int. Cl.³ .............................................. C07C 7/12
[52] U.S. Cl. ..................................... 585/828; 585/826
[58] Field of Search .............................. 585/828, 826; 208/310 Z

[56] References Cited

U.S. PATENT DOCUMENTS

| | | | |
|---|---|---|---|
| 3,696,107 | 10/1972 | Neuzil | 585/828 X |
| 3,715,409 | 2/1973 | Broughton | 585/828 X |
| 3,761,533 | 9/1973 | Otani et al. | 585/828 X |

*Primary Examiner*—Delbert E. Gantz
*Assistant Examiner*—William Leader
*Attorney, Agent, or Firm*—James R. Hoatson, Jr.; Louis A. Morris; William H. Page, II

[57] ABSTRACT

A process for separating a first component comprising meta-xylene, a second component comprising a mixture of para-xylene and ortho-xylene and a third component comprising ethyl benzene from a feedstream employing an adsorbent comprising a Y-zeolite containing sodium ions at exchangeable cationic sites and a desorbent material comprising toluene which in combination have selectivities for the first, second and third components, respectively, in descending order of magnitude. The process uses a simulated-moving bed counter current flow system with an intermediate raffinate stream taken off the column at about the midpoint of the adsorption zone in addition to the usual extract and raffinate product streams.

4 Claims, No Drawings

PRODUCTION OF PURE M-XYLENE AND PURE ETHYL BENZENE FROM A MIXTURE OF C8 AROMATIC ISOMERS

CROSS-REFERENCE TO RELATED APPLICATION

This application is a continuation-in-part of my prior, co-pending application Ser. No. 123,227 filed Feb. 7, 1980. All of the teachings of this prior application are incorporated herein by reference.

BACKGROUND OF THE INVENTION

1. Field of the Invention

The field of art to which the claimed invention pertains is solid bed adsorptive separation processes. More specifically, the invention relates to a process and particular flow scheme for separating $C_8$ aromatic isomers from a mixture thereof.

2. Description of the Prior Art

It is well known in the separation art that certain crystalline aluminosilicates can be used to separate one hydrocarbon type from another hydrocarbon type. The separation of normal paraffins from branched chained paraffins for example can be accomplished by using a type A zeolite which has pore openings from 3 to 5 Angstroms. Such a separation process is disclosed in U.S. Pat. Nos. 2,985,589 and 3,201,491. These adsorbents allow a separation based on the physical size difference in the molecules by allowing the smaller or normal hydrocarbons to be passed into the cavities within the zeolite adsorbent, while excluding the larger or branched chain molecules. U.S. Pat. Nos. 3,265,750 and 3,510,423 for example disclose processes in which larger pore diameter zeolites such as the type X or type Y structured zeolites can be used to separate olefinic hydrocarbons from non-olefinic hydrocarbons.

In addition to being used in processes for separating hydrocarbon types, adsorbents comprising type X or Y zeolites have also been employed in processes to separate individual hydrocarbon isomers. In the processes described in U.S. Pat. Nos. 3,558,730; 3,558,732; 3,626,020 and 3,686,342 for example particular zeolitic adsorbents are used to separate desired xylene isomers; in U.S. Pat. No. 3,114,782 they are used to separate alkyl-trisubstituted benzenes; in U.S. Pat. No. 3,864,416 they are used to separate tetraalkyl substituted aromatic hydrocarbon isomers and in U.S. Pat. No. 2,668,267 they are used to separate particular alkyl substituted naphthalenes.

The principal of the simulated moving bed to continuously separate the components of the fluid mixture by contact with a solid adsorbent is as set forth in D. B. Broughton U.S. Pat. No. 2,985,589, hereby incorporated herein by reference thereto. The simulated moving bed functions by periodically advancing through the column of adsorbent the various points of introducing and withdrawing the liquid streams.

A common problem with the simulated moving bed flow scheme is that the raffinate itself contains components the separation of which is desired, but which cannot be separated by conventional means, such as fractionation. In such cases, therefore, it has been the practice to provide a second stage simulated moving bed to achieve the complete separation. I have discovered a method of operating a simulated moving bed column which avoids the aforementioned problem that would otherwise occur with certain three component feedstocks.

The process is particularly useful in separating ethylbenzene and ortho, meta, and para-xylene from a mixture in which they occur.

SUMMARY OF THE INVENTION

It is, accordingly, a broad objective of my invention to provide a process for separating a first component comprising meta-xylene, a second component comprising a mixture of para-xylene and ortho-xylene, and a third component comprising ethyl benzene from a fluid feed stream comprising a mixture of those components, which process employs an adsorbent comprising a Y-zeolite containing sodium ions at exchangeable cationic sites and a desorbent material comprising toluene which in combination exhibit relative selectivities for the first, second, and third components, respectively, in descending order of magnitude. The process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone being defined by the adsorbent located between a feed input stream at an upstream boundary of the zone and a raffinate output stream at a downstream boundary of the zone; (c) maintaining a purification zone immediately upstream from the adsorption zone, the purification zone being defined by the adsorbent located between an extract output stream at an upstream boundary of the purification zone and the feed input stream at a downstream boundary of the purification zone; (d) maintaining a desorption zone immediately upstream from the purification zone, the desorption zone being defined by the adsorbent located between a desorbent input stream at an upstream boundary of the zone and the extract output stream at a downstream boundary of the zone; (e) passing the feed stream into the adsorption zone at adsorption conditions to effect the selective adsorption of the first component by the adsorbent in the adsorption zone and withdrawing a raffinate output stream from the adsorption zone; (f) passing a desorbent material into the desorption zone at desorption conditions to effect the displacement of the first component from the adsorbent in the desorption zone; (g) withdrawing an extract stream comprising the first component and desorbent material from the desorption zone; (h) withdrawing a raffinate output stream comprising the third component and desorbent material from the adsorption zone at the downstream boundary thereof; (i) withdrawing an intermediate raffinate stream comprising a mixture of the second component, the third component and desorbent material from the adsorption zone at a locus approximately midway between the upstream and downstream boundaries of the zone; and (j) periodically advancing through the column of adsorbent in a downstream direction with respect to fluid in the adsorption zone, the feed input stream, raffinate output stream, desorbent input stream, extract output stream and the intermediate raffinate output stream to effect the shifting of zones through the adsorbent and the production of extract output, raffinate output and intermediate raffinate output streams.

DESCRIPTION OF THE INVENTION

At the outset the definitions of various terms used throughout this specification will be useful in making clear the operation, objects and advantages of my process.

A "feed mixture" is a mixture containing one or more extract components and one or more raffinate components to be fed to the adsorbent of my process. The term "feed streams" indicates a stream of feed mixture which passes to the adsorbent used in my process.

An "extract component" is a type of compound or a compound, such as an aromatic isomer, that is more selectively adsorbed by the adsorbent while a "raffinate component" is a compound or type of compound that is less selectively adsorbed. The selectivity of the adsorbent for an "intermediate raffinate component" lies between that for the extract and raffinate components. In this process, meta-xylene is the extract component, and ethyl benzene, and ortho and para-xylene are the raffinate components. The term "raffinate stream" or "raffinate output stream" means a stream through which a raffinate component is removed from an adsorbent. There are two raffinate streams in the process of this invention, the usual stream taken from the downstream boundary of the adsorption zone and an intermediate stream taken from about midpoint of the adsorption zone. The composition of a raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in a raffinate stream. The extract and raffinate streams then are further distinguished from each other and from the feed mixture by the ratio of the concentrations of an extract component and a specific raffinate component, both appearing in the particular stream. For example the ratio of concentration of the more selectively adsorbed meta-xylene to the concentration of less selectively adsorbed isomers and ethyl benzene will be highest in the extract stream, next highest in the feed mixture, next highest in the intermediate stream, and lowest in the raffinate stream. Likewise, the ratio of the less selectively adsorbed isomer and ethyl-benzene to the more selectively adsorbed meta-xylene will be highest in the raffinate stream, next highest in the intermediate raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate streams contain desorbent materials, at least a portion of the extract stream and preferably at least a portion of the raffinate streams from the adsorbent will be passed to separation means, typically fractionators, where at least a portion of desorbent material will be separated at separating conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "non-selective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into the process for efficient operation to take place for a given quantity of adsorbent. When adsorbent "passes" into an operational zone (which zones are used in a preferred embodiment of this process and are hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume of adsorbent material passing into that zone, there is a net entrainment of liquid into the zone by the adsorbent. Since this net entrainment is a fluid present in non-selective void volume of the adsorbent, it in most instances comprises less selectively retained feed mixture components. The selective pore volume of an adsorbent can in certain instances adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be utilized in the process of this invention will comprise a mixture of the xylene isomers and ethyl benzene. The adsorbent-desorbent combination chosen for use in this process, Y-zeolite containing sodium ions at exchangeable cationic sites and toluene, respectively, exhibits highest relative selectively for meta-xylene, next highest for para-xylene and ortho-xylene and lowest for ethyl benzene.

To effect the separation of this invention the feed mixture is contacted with the adsorbent and the component having the highest relative selectivity is more selectively adsorbed and retained by the adsorbent while the other components are relatively unadsorbed and are removed from the interstitial void spaces between the particles of adsorbent and the surface of the adsorbent. The adsorbent containing the more selectively adsorbed component is referred to as a "rich" adsorbent-rich in the more selectively adsorbed component. The adsorbed component is then recovered from the rich adsorbent by contacting the rich adsorbent with a desorbent material.

The term "desorbent material" generally means any fluid substance capable of removing a selectively adsorbed feed component from the adsorbent. In the swing-bed system in which the selectively adsorbed feed component is removed from the adsorbent by a purge stream desorbent material selection is not too critical and desorbent material comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated continuously at substantially constant pressures and temperatures to insure liquid phase, the desorbent material relied upon must be judiciously selected to satisfy several criteria. First the desorbent material must displace the extract components from the adsorbent with reasonable mass flow rates without itself being so strongly adsorbed as to unduly prevent the extract component from displacing the desorbent material in a following adsorption cycle. Expressed in terms of the selectively (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent material to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent admixture with desorbent material and without a method of separating at least a portion of desorbent material, such as distillation, neither the purity of the extract product nor the purity of the raffinate product would be very high. It is therefore contemplated that any desorbent material will have substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling point between the desorbent material and the feed mixture shall be at least about 5° C. The boiling range of the desorbent material may be higher or lower than that of the feed mixture. The desorbent material chosen as most suitable for use in this process is toluene.

The prior art has recognized that certain characteristics of adsorbents are highly desirable, if not absolutely necessary, to the successful operation of a selective adsorption process. Among such characteristics are: adsorptive capacity for some volume of an extract component per volume of adsorption; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } D]_U}$$

where C and D are two components of the feed represented in volume percent and the subscripts A and U represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) become less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

To best evaluate promising adsorbent systems and to translate this type of data into a practical separation process requires actual testing of the best system in a continuous countercurrent liquid solid contacting device. The general operating principles of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and the raffinate and extract streams are being withdrawn through two more. All remaining access lines are inactive and when the position of the distributing valve is advanced by one index all active positions will be advanced by one bed. This stimulates a condition in which the adsorbent physically moves in a direction countercurrent to the liquid flow. Additional details on the above-mentioned adsorbent testing apparatus and adsorbent evaluation techniques may be found in the paper "separation of $C_8$ Aromatics by Adsorption" by A. J. deRosset, R. W. Neuzil, D. J. Korous and D. H. Rosback presented at the American Chemical Society, Los Angeles, Calif., Mar. 28 through Apr. 2, 1971. The preceding references are incorporated herein by reference thereto.

Adsorbents generally known to be useful in aromatic isomers separation process comprise specific crystalline aluminosilicates or molecular sieves. Particular crystalline aluminosilicates include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" athough widely used is not strictly suitable since the separation of specific aromatic isomers is apparently dependent on differences in electrochemical attraction of the different isomers and the adsorbent rather than on pure physical size differences in the isomer molecules.

In hydrated form, the crystalline aluminosilicates generally encompass those zeolites represented by the formula 1 below:

$$M_{2/n}O{:}Al_2O_3{:}wSiO_2{:}yH_2O \qquad \text{Formula 1}$$

where "M" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The prior art has generally recognized that adsorbents comprising the type X and the type Y zeolites can be used in certain adsorptive separation processes. These zeolites are described and defined in U.S. Pat. Nos. 2,882,244 and 3,120,007 respectively.

The type X structured zeolite in the hydrated or partially hydrated form can be represented in terms of mole oxides as shown in formula 2 below:

$$(0.9 \pm 0.2)M_{2/n}O{:}Al_2O_3{:}(2.5 \pm 0.5)SiO_2{:}yH_2O \qquad \text{Formula 2}$$

where "M" represents at least one cation having a valence of not more than 3, "n" represents the valence of "M", and "y" is a value up to about 9 depending upon the identity of "M" and the degree of hydration of the crystal. As noted from Formula 2 the $SiO_2/Al_2O_3$ mole ratio is $2.5\pm0.5$. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominately sodium and the zeolite is therefore referred to as a sodium type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in formula 3 below:

$$(0.9 \pm 0.2)M_{2/n}O{:}Al_2O_3{:}wSiO_2{:}yH_2O \qquad \text{Formula 3}$$

where "M" is at least one cation having a valence not more than 3, "n" represents the valence of "M", "w" is a value greater than about 3 up to 6, and "y" is a value up to about 9 depending upon the identity of "M", and the degree of hydration of the crystal. The $SiO_2/Al_2O_3$ mole ratio for type Y structured zeolites can thus be from about 3 to about 6. Like the type X structured zeolite, the cation "M" may be one or more of a variety of cations but, as the type Y zeolite is initially prepared, the cation "M" is also usually predominately sodium. The type Y zeolite containing predominately sodium cations at the exchangeable cationic sites is therefore referred to as a sodium type Y zeolite.

Cations occupying exchangeable cationic sites in the zeolite may be replaced with other cations by ion exchange methods generally known to those have ordinary skill in the field of crystalline aluminosilicates. Such methods are generally performed by contacting the zeolite or a base material containing the zeolite with an aqueous solution of the soluble salt of the cation or cations desired to be placed upon the zeolite. After the desired degree of exchange takes place the sieves are removed from the aqueous solution, washed, and dried to a desired water content. By such methods the sodium cations and any nonsodium cations which might be occupying exchangeable sites as impurities in sodium-type X or sodium-type Y zeolite can be partially or essentially completely replaced with other cations.

The term "base material" as used herein shall refer to a material containing an X or a Y zeolite and amorphous material which can be used to make the adsorbents used in my process. The zeolite will typically be present in the base material in amounts ranging from about 75 wt. % to about 98 wt. % of the base material based on volatile free composition. Volatile free compositions are generally determined after the base material has been calcined at 900° C. in order to drive off all volatile matter. The remainder of the base material will generally be amorphous material such as silica, alumina or silica-alumina mixtures or compounds, such as clays, which material is present in intimate mixture with the small particles of the zeolite material. This amorphous material may be an adjunct of the manufacturing process for X or Y zeolite (for example, intentionally incomplete purification of either zeolite during its manufacture) or it may be added to relatively pure X or Y zeolite but in either case its usual purpose is as a binder to aid in forming or agglomerating the hard crystalline particles of the zeolite. Normally the base material will be in the form of particles such as extrudates, aggregates, tablets, macrospheres or granules having a desired particle size range. The adsorbent used in my process will preferably have a particle size range of about 16-60 mesh (Standard U.S. Mesh). Examples of suitable base materials which can be used to make the adsorbents employed in my process are "Molecule Sieves 13X" and "SK-40" both of which are available from the Linde Company, Tonawanda, New York. The first material of course contains X zeolite while the latter material contains Y zeolite.

I have observed that the adsorbent that demonstrates the best selectivity for the meta-xylene is a Y zeolite containing sodium at exchangeable cationic sites. Adsorbents for this process will preferably be in a particle size range of from about 20 to about 60 U.S. mesh. Maintaining adsorbent water content within a range of from about 2 to about 7 wt. % has been found to be necessary to maintain optimum adsorbent and process performance and water may be added to or removed from the process during operations as necessary to maintain this range. By knowing the initial water content of the adsorbent and by analyzing the process input and output stream for water content the water content of the adsorbent during process operation can be calculated. Water may be added to the adsorbent if necessary either on an intermittent or more preferably on a continuous basis by itself or in admixture with feed or desorbent material to maintain the desired concentration of water on the adsorbent. Water may be removed from the adsorbent if necessary by passing a very dry feed stream to the process and allowing the output streams to remove some water from the adsorbent until the desired range is achieved.

The adsorbent is employed in a countercurrent moving-bed or simulated moving-bed countercurrent flow system. With the moving-bed or simulated moving-bed flow systems a feed mixture and a desorbent material are continuously fed to the process and adsorption and desorption are continuously taking place which allows continuous production of an extract output stream and raffinate output streams. The basic operating principles and sequence of operation of one such simulated moving-bed countercurrent flow system are described in U.S. Pat. No. 2,985,589 incorporated herein by reference thereto. My invention utilizes the system described in U.S. Pat. No. 2,985,589, except for the provision in my invention for withdrawal of the additional intermediate raffinate stream. In such a system it is the progressive movement of multiple liquid access points down an adsorbent chamber that simulates the upward movement of an adsorbent contained in the chamber. Only five of the access lines are active at any one time; the feed input stream, desorbent inlet stream, raffinate and intermediate raffinate outlet streams, and extract outlet stream access lines. Coincident with this simulated upward movement of a solid adsorbent is the movement of a liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divided the adsorbent chamber into separate zones, each of which has a different function. In this embodiment of my process it is generally necessary that three separate operational zones to be present in order for the desired operations to take place although in some instances an operational fourth zone may be used.

The adsorption zone, zone 1, defined as the adsorbent located between a feed inlet stream and a raffinate outlet stream. In this zone, a feed mixture contacts an adsorbent, an extract component is adsorbed, and a raffinate stream is withdrawn at the downstream boundary of the zone. The intermediate raffinate stream is withdrawn from the adsorption zone at a locus approximately midway between the upstream and downstream boundaries of the zone. Since the general flow through zone 1 is from the feed stream which passes into the zone to the raffinate streams which pass out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the absorbent between an extract outlet stream and the feed inlet stream. The basic operation taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 (hereinafter described) into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3.

The desorption zone is defined as the adsorbent between a desorbent inlet stream and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream at the downstream boundary of zone 1 and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating the extract stream removed from zone 3. In the instances in which the fourth operational zone is not utilized the raffinate stream passed from zone 1 to zone 3 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of an adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the absorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents incorporated herein by reference thereto, disclose a rotary type connection valve in which the suitable advancement of the various input and output streams from fixed sources can be achieved without difficulty.

In many instances, one operational zone will contain a much larger quantity of an adsorbent than some other operation zone. For instance, in some operations the buffer zone can contain a minor amount of an adsorbent as compared to the adsorbent required for the adsorption and purification zones. It can also be seen that when a very efficient desorbent material is used which can easily desorb an extract component from an adsorbent, it is possible that a relatively small amount of adsorbent will be needed in a desorption zone as compared to the adsorbent needed in the buffer zone or adsorption zone or purification zone. It is not required that an absorbent be located in a single column which is divided into zones, and the use of multiple chambers or a series of columns is also within the scope of this embodiment.

It is not necessary that all of the input or output streams be simultaneously used, and in fact, in many instances some of the streams can be shut off while others effect an input or output of material. One apparatus which can be utilized to effect the process of this invention in a preferred embodiment will contain a series of individual beds connected by connecting conduits upon which are placed input and output taps to which the various input and output streams can be attached and alternatively and periodically shifted to effect continuous operation. In some instances, the connecting conduits can be connected to transfer taps which during the normal operations function intermittently as a conduit through which material passes into or out of the process.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of each raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate products will be less than about 5 vol. % and more preferably less than about 1 vol %. The separation means will typically be a fractionation column, the design and operation of which is well known to the separation art.

Reference can be made to D. B. Broughton U.S. Pat. No. 2,985,589 and to a paper entitled "Continuous Adsorptive Processing A New Separation Technique" by D. B. Broughton presented at the 34th Annul Meeting of the Society of Chemical Engineers at Tokyo, Japan on Apr. 2, 1969, incorporated herein by reference thereto for further explanation of the simulated moving-bed countercurrent process flow scheme.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vapor-phase operation. Adsorption conditions will include a temperature range of from about 20° C. to about 250° C. with about 100° C. to about 200° C. being more preferred and a pressure range of from about atmospheric to about 500 psig. with from about atmospheric to about 250 psig. being more preferred to insure liquid phase. Desorption conditions will include the same range of temperatures and pressures as used for adsorption conditions.

The size of the units which can utilize the process of this invention can vary anywhere from those of pilot-plant scale (see for example my assignee's U.S. Pat. No. 3,706,812) to those of commercial scale and can range in flow rates from as little as a few cc an hour to many thousands of gallons per hour.

The following illustrative embodiment is presented for illustration purposes and more specifically is presented to illustrate the selectivity relationships that make the process of my invention possible. Reference to specific cations, desorbent materials, feed mixtures and operating conditions is not intended to unduly restrict the scope and spirit of the claims attached hereto.

ILLUSTRATIVE EMBODIMENT

This illustrative embodiment illustrates the preferred embodiment of the present invention in which the feed stream comprises a mixture of ethyl benzene and ortho, meta and para-xylene. The desorbent used is toluene, and the adsorbent used is Y-zeolite with sodium as the predominant cation. The relative selectivities for this system are as follows:

|  | $\beta$ |
|---|---|
| meta-xylene | 1.80 |
| para-xylene | 1.00 |
| ortho-xylene | 1.00 |
| ethyl benzene | 0.44 |

With reference to my invention as claimed, meta-xylene is the first component, a mixture of para-xylene and ortho-xylene the second component, and ethyl benzene is the third component. The first component comprises the extract stream, a mixture of the second and third components the intermediate raffinate stream, and the third component the raffinate stream. The following is a representative material balance illustrative of the invention.

MATERIAL BALANCE

|  | Feed | Extract | Raff. | Intermediate Raffinate |
|---|---|---|---|---|
| Meta-xylene | 45 | 44.8 | 0.00 | 0.20 |
| Para-xylene | 20 | 0.1 | 0.05 | 19.85 |
| Ortho-xylene | 15 | 0.1 | 0.05 | 14.85 |
| Ethyl Benzene | 20 | 0.0 | 12.00 | 8.00 |
|  | 100 | 45.0 | 12.10 | 42.90 |

Since the ethyl benzene comprising the raffinate stream is free of meta-xylene and essentially pure, the raffinate stream may be passed to an isomerization unit for conversion of the ethyl benzene to xylene.

I claim as my Invention:

1. A process for separating a first component comprising meta-xylene, a second component comprising a mixture of para-xylene and ortho-xylene, and a third component comprising ethyl benzene from a fluid feed stream comprising a mixture of said components, which process employs an adsorbent comprising a Y-zeolite containing sodium ions at exchangeable cationic sites and a desorbent material comprising toluene which in combination exhibit relative selectivities for said first, second and third components, respectively, in descending order of magnitude, which process comprises the steps of:
   (a) maintaining net fluid flow through a column of said adsorbent in a single direction, which column contains at least three zones having separate operational functions occurring therein and being serially interconnected with the terminal zones of said column connected to provide a continuous connection of said zones;
   (b) maintaining an absorption zone in said column, said zone defined by the adsorbent located between a feed input stream at an upstream boundary of said zone and a raffinate output stream at a downstream boundary of said zone;
   (c) maintaining a purification zone immediately upstream from said adsorption zone, said purification zone defined by the adsorbent located between an extract output stream at an upstream boundary of said purification zone and said feed input stream at a downstream boundary of said purification zone;
   (d) maintaining a desorption zone immediately upstream from said purification zone, said desorption zone defined by the adsorbent located between a desorbent input stream at an upstream boundary of said desorption zone and said extract output stream at a downstream boundary of said desorption zone;
   (e) passing said feed stream into said adsorption zone at adsorption conditions to effect the selective adsorption of said first component by said adsorbent in said adsorption zone and withdrawing said raffinate output stream from said adsorption zone;
   (f) passing said desorbent material into said desorption zone at desorption conditions to effect the displacement of said first component from the adsorbent in said desorption zone;
   (g) withdrawing said extract stream comprising said first component and desorbent material from said desorption zone;
   (h) withdrawing said raffinate output comprising a stream of substantially pure third component and desorbent material from said adsorption zone at said downstream boundary thereof;
   (i) withdrawing an intermediate raffinate stream comprising a mixture of said second component, said third component, and desorbent material from said adsorption zone in an amount sufficient to provide said substantially pure third component raffinate stream in admixture with said desorbent material withdrawn in (h), said intermediate raffinate stream being withdrawn at a locus approximately midway between the upstream and downstream boundaries of said adsorption zone; and
   (j) periodically advancing through said column of adsorbent in a downstream direction with respect to fluid flow in said adsorption zone the feed input stream, raffinate output stream, desorbent input stream, extract output stream and the intermediate raffinate output stream to effect the shifting of zones through said adsorbent and the production of extract output, raffinate output and intermediate raffinate output streams.

2. The process of claim 1 wherein in the adsorption and desorption conditions include a temperature within the range of from about 20° C. to about 250° C. and a pressure within the range of from about atmospheric to about 500 psig to achieve liquid phase.

3. The process of claim 1 wherein at least portions of said raffinate output stream, said extract output stream and said intermediate raffinate output stream are each passed to separate separation means wherein at least a portion of said desorbent material is separated from each such stream to produce raffinate, extract and intermediate raffinate products.

4. The process of claim 1 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

* * * * *